United States Patent [19]

Frantz et al.

[11] Patent Number: 5,536,496
[45] Date of Patent: Jul. 16, 1996

[54] PASTEURELLA MULTOCIDA TOXOID VACCINES

[75] Inventors: Joseph C. Frantz; David S. Roberts; Leroy A. Swearingin, all of Lincoln; Richard J. Kemmy, Gretna, all of Nebr.

[73] Assignee: Pfizer Inc., New York, N.Y.

[21] Appl. No.: 439,714

[22] Filed: May 12, 1995

Related U.S. Application Data

[63] Continuation of Ser. No. 87,946, Jul. 6, 1993, abandoned, which is a continuation of Ser. No. 537,454, Jun. 13, 1990, abandoned.

[51] Int. Cl.$^6$ .................. A61K 39/02; A61K 39/00; A61K 39/02; C07K 14/285
[52] U.S. Cl. .................. 424/236.1; 424/184.1; 424/254.1; 424/255.1; 530/350
[58] Field of Search .................. 424/236.1, 240.1; 530/350

[56] References Cited

PUBLICATIONS

T. Nakai, *Research in Veterinary Science* 1987, "Purification of three fragments of the dermonecrotic toxin from *Pasteurella multocida*", 42, 232–237.
*Microbiology*, Section III, Medical Bacteriology, pp. 518–519.
Zinsser, Microbiology, ed. Joklik et al, Appleton–Century–Crofts, New York, pp. 791–793 (1980).
M. Kobisch et al, Vet. Record, 124:57–61 (1989).
N. T. Foged et al, Vet. Record, 125:7–11 (1989).
K. Barfod et al, Nord. Vet. Med., 36:337–345 (1981).
N. Chanter et al, J. Gen. Microbiol., 132:1089–1097 (1986).
N. Cheville et al., Vet. Pathol., 25:518–520 (1988).
E. Kamp et al, Vet. Microbiol. 13:235–248 (1987).
J. C. Baars et al, Abstract of "Challenge and Field Experiments with an Experimental Atrophic Rhinitis Vaccine, Containing *Pasteurella multocida* DNT–Toxoid and *Bordetella bronchisetica* In Proceedings", Intn'l. Pig Vet. Soc., 9th Congress, p. 247 (1986).
M. F. deJong et al, Abstract of "Neutralization Test Against AR–toxin of *Pasteurella multocida* in Pig Herds after Vaccination with AR–Vaccines" In Proceedings, Intn'l. Pig Vet. Soc., 9th Congress Barcelona, Spain), p. 221 (1986).
Petersen et al, Inf & Im 57:3907–13 1989.
Vedros et al Workshop Abstract 13th Ann. Conf. & Workshop & 7th Eastern Fish health workshop May 9–13 1982.
Nakai et al. I & I 46: 429–434 1984 Purification of Dermonecrotic Toxin from a Sonic Extract of *P. multocida* SP–72 Serotype D.
J. M. Rutter et al, Vet. Res., 114:89–90 (1984).
J. Descamps et al, "Vaccination Study for Protection Against the Dermonecrotic Toxin of *Pasteurella multocida* Type D", Proceedings 9th International Pig Veterinary Society Congress, p. 241 (1986).
deJong et al, Proceedings of 8th International Pig Veterinary Society Congress, p. 161 (1984).
Niwa et al J. of Bact. Alteration of Physical, Chemical, & Biological properties of endotoxin by treatment with mild alkali 1069–1077. 1969.
M. Kobisch et al, Abstract of "An Evaluation of NOBI–VAC AR and an Experimental Atrophic Rhinitis Vaccine, Containing *Pasteurella multocida* DNT–Toxoid & *Bordetella bronchiseptica*, In Pigs", In Proceedings, Intn'l. Pig Veterinary Society 9th Congress (Barcelona, Spain), p. 246 (1986).
T. Nakai et al. Am. J. Vet. Res., 45:2410–2413 (1984).
T. Nakai 45:429–434 (1984).
T. Nakai et al, Abstract of "Purification of Dermonecrotic Toxin from a Sonic Extract of *Pasteurella multocida* or *Bordetella bronchiseptica*", In Proceedings, Intn'l. Pig Vet. Soc. 9th Congress (Barcelona, Spain) p. 222 (1986).
K. Pedersen et al, Nord. Vet. Med., 33:513–522 (1981).
K. Pedersen et al, Nord. Vet. Med., 31:293–302 (1982).
A.M.M.A. Pennings et al, Vet. Microb., 9:503–508 (1984).
C. Pijoan, "Atrophic Rhinitis Today" In Proceedings, Amer. Asso. of Swine Practitioners, St. Louis, MO, 139–144 (1988).
R. Rimler et al. Am. J. Vet. Res., 47:730–737 (1986).
J. M. Rutter et al, Vet. Rec., 114:393–396 (1984).
J. M. Rutter, Res. Vet. Sci., 34:287–295 (1983).
Deutscher Guide to Protein Purification 1990, pp. 290–296.
Encyclopedia & Dictionary of Medicine, Nursery, & Allied Health, p. 1011.

*Primary Examiner*—Hazel F. Sidberry
*Attorney, Agent, or Firm*—Peter C. Richardson; Paul H. Ginsburg; Lorraine B. Ling

[57] ABSTRACT

This invention provides vaccine compositions, methods of producing same and methods for protecting porcine animals against disease associated with infection by toxigenic *Pasteurella multocida*. The vaccines of this invention contain effective amounts of a free, soluble *P. multocida* toxoid and/or a *P. multocida* bacterin with a cell-bound toxoid.

6 Claims, No Drawings

PASTEURELLA MULTOCIDA TOXOID VACCINES

This is a continuation of application Ser. No. 08/087,946, filed on Jul. 6, 1993, now abandoned, which is a continuation of application Ser. No. 07/537,454, filed Jun. 13, 1990, now abandoned.

FIELD OF THE INVENTION

This invention is generally in the field of veterinary vaccines, vaccine compositions, and methods of producing same. More particularly, this invention relates to vaccine compositions and methods for protecting animals against diseases associated with infection by toxigenic strains of *Pasteurella multocida*.

BACKGROUND OF THE INVENTION

*Pasteurella multocida* has been associated with disease in many species of animals, including man and bovine, ovine and porcine animals. It typically affects the nasopharyngeal regions and lungs of infected animals. For example, toxigenic strains of *P. multocida*, capsular type A or D, cause atrophic rhinitis in swine. Atrophic rhinitis (AR) results in severe necrosis of the epithelia of the upper respiratory tract as well as deformities and atrophy of the turbinates and snouts of pigs.

The pathogenicity of *P. multocida* is due in large part to the production of a potent necrotizing toxin, also called dermonecrotic toxin (DNT), which will be referred to hereinafter as "the toxin". The toxin has been characterized as a heat-labile protein with a molecular weight of approximately 140,000 to 160,000.

*P. multocida* is distinguishable from other species of Pasteurella on the basis of its growth characteristics, as follows: hemolysis: negative (90%); growth on MacConkey's agar: negative; indole production: positive; urease production: negative; and mannitol metabolism: positive. See, Zinsser, *Microbiology*, edit. by Joklik et al., Appleton-Century-Crofts, New York, 1980, pages 791–793, which is incorporated herein by reference.

Currently available vaccines for protecting animals from diseases associated with infection by *P. multocida* include inactivated toxigenic *P. multocida* cells, inactivated preparations of partly purified *P. multocida* toxin and combinations of *P. multocida* cell-free preparations with other inactivated *P. multocida* strains or *B. bronchiseptica* strains. [See, e.g., M. Kobisch et al, *Vet. Record*, 124:57–61 (1989); and N. T. Foged et al, *Vet. Record*, 125:7–11 (1989)]. These vaccine preparations, however, are not fully protective against disease because they fail to elicit effective amounts of the antibody that neutralizes the toxin, known as "antitoxin".

There remains a need in the art of veterinary practice for effective vaccines against infection of animals by toxigenic *P. multocida*.

SUMMARY OF THE INVENTION

The present invention provides novel vaccine compositions and components which protect animals against disease associated with infection by toxigenic *Pasteurella multocida*. These vaccine compositions are characterized by the ability to elicit significant quantities of circulating antitoxin.

In a first aspect, this invention provides a vaccine which comprises an immunogenic amount of a stable, soluble, cell-free toxoid of *P. multocida*, and a carrier suitable for internal administration. This novel *P. multocida* toxoid is produced by a method that employs subjection of the toxin to varying pH and temperature, which method is also a novel aspect of the present invention. The term "toxoid" describes a preparation of the toxin that has been inactivated ("toxoided") by a process that abolishes its toxicity without destroying its ability to induce the production of the specific neutralizing antitoxin.

In another aspect, the invention provides a novel vaccine composition containing a whole *Pasteurella multocida* bacterin with cell-bound toxoid. This composition can induce in a previously unvaccinated animal a superior antitoxin response compared to the free, soluble toxoid. This composition is also preferably associated with a carrier suitable for internal administration.

In still another aspect, the invention provides a novel vaccine composition comprising (1) a whole *Pasteurella multocida* bacterin with cell-bound toxoid which, upon internal administration to an animal, induces an antitoxin response, and (2) the free toxoid of *P. multocida*. This vaccine composition produces an unexpected synergistic antitoxin response, much greater than the sum of the separate effects of the two components. A carrier is also desirably associated with this composition.

In a further aspect the above three vaccine compositions may be varied by combination with an immunogenic amount of one or more additional antigens. Such additional antigens may include, among others, a *B. bronchiseptica* bacterin or an *Erysipelothrix rhusiopathiae* bacterin. Other conventional vaccine components may also be added to the vaccine compositions of this invention.

Another aspect of this invention includes a vaccine dosage unit of each of the above vaccine compositions. One embodiment of the invention includes a vaccine dosage unit comprising 0.5 to 3 mL of a sterile solution of an immunogenic amount of a *P. multocida* toxoid. Another embodiment includes a dosage unit of 0.5 to 3 mL of a sterile suspension of an immunogenic amount of a *P. multocida* bacterin with cell-bound toxoid which upon internal administration to an animal induces an antitoxin response. Still another embodiment is a dosage unit comprising 0.5 to 3 mL of a sterile mixture of the free and cell-bound toxoids. A further embodiment is a dosage unit comprising 0.5 to 3 mL of a sterile mixture of immunogenic amounts of the free and cell-bound toxoids and one or more additional antigenic components.

In yet another aspect, the invention provides a method for detoxifying the *P. multocida* toxin to prepare a free, soluble immunogenic toxoid which comprises incubating the toxin at a pH greater than 9 for at least 12 hours.

A further aspect of the invention provides a method for detoxifying a whole *P. multocida* culture in which the toxin is completely converted to a stable toxoid within the bacterial cells, for use as a vaccine. This method involves treating the culture with a suitable concentration of formaldehyde, at a suitable temperature and for a sufficient time.

Yet a further aspect of this invention is a method for vaccinating an animal against *P. multocida* which comprises internally administering to the animal an effective amount of one or more of the vaccine compositions described above.

Other aspects and advantages of the present invention are described further in the following detailed description of preferred embodiments thereof.

DETAILED DESCRIPTION OF THE INVENTION

The present invention provides vaccine compositions useful in the prophylaxis of diseases resulting from infections with toxigenic *P. multocida*, non-toxigenic strains of *P. multocida*, and other pathogenic organisms. Such diseases include atrophic rhinitis (AR), pleuritic and pneumonic pasteurellosis, and erysipelas, among others.

One embodiment of this invention is a vaccine which comprises a free, soluble *P. multocida* toxoid in a suitable carrier. The toxoid of this invention is prepared generally by extracting toxin from the bacterial cells and causing a partial denaturation by incubating the cell-free toxin for about 12 to 24 hours at a pH greater than 9, at an incubation temperature of between about 12° C. to 19° C.

More specifically, the free toxoid of this invention is prepared as follows: A selected toxigenic *P. multocida* strain is grown in a suitable culture medium. At the end of the growth cycle, the toxin is liberated from the cells by conventional physical or chemical means e.g., french press or sonic disruption, and cellular debris is removed by centrifugation and filtration. The cell-free extracted toxin is then incubated, preferably at pH of about 10.5, at ambient or slightly cooler temperature for preferably 18 hours. Following this incubation, the pH is adjusted to neutrality. This process results in complete detoxification of the toxin, providing a toxoid soluble in aqueous solutions (e.g. phosphate buffered saline, tris buffered saline).

The soluble *P. multocida* toxoid preparation of this invention is both antigenic and immunogenic. Specifically, the soluble toxoid can elicit antibodies that can bind to the toxin, and neutralize its toxicity. Further, the soluble toxoid of this invention is characteristically stable at 4° C. for at least 24 months, which is a highly advantageous commercial characteristic, indicating that this vaccine may be stored for later use.

As another embodiment of this invention there is provided a whole bacterin-toxoid of *P. multocida* which contains the toxoid encapsulated and stabilized within the bacterial cell. The bacterin toxoid is prepared from a culture that is still growing exponentially and that has not yet begun to release the toxin into the growth medium. Formalin (formaldelhyde solution USP) is added at a concentration of 0.5% v/v and inactivation is continued at about 37° C. for 4 days. Other formalin concentrations may be employed in this method. However a higher concentration will require a shorter inactivating incubation period, and a lower concentration will require a longer inactivating incubation period. One of skill in the art can readily determine these parameters based on this disclosure. The toxoid is thereby encapsulated within the bacterial cell. The dead bacterial cells, with the toxoid sequestered safely within, are ideal antigenic particles for presentation to those host cells that mediate the immunizing process. This is especially important for animals that have not previously been exposed to the toxin or the toxoid and that totally lack antitoxin.

In the *P. multocida* bacterin-toxoid of this invention the cell-bound toxoid is remarkably stable. Loss of antigenic potency was undetectable after storage at 4° C. for more than two years.

For purposes of this invention, any toxigenic strain of *P. multocida* may be used to provide the free toxoid or the bacterin-toxoid of this invention. The free or cell-bound toxoids described above can be derived from any strain of *P. multocida* which elaborates dermonecrotic toxin. Several such strains are available, e.g., from the American Type Culture Collection, Rockville, Md. or from a variety of veterinary colleges or laboratories. The strain used below in the examples is *P. multocida*, type D, strain 8, which is available, upon request, from the University of Illinois.

Suitable culture media for use in growing the *P. multocida* cultures may be selected by one of skill in the art, but preferably includes, without limitation, the medium described by Herriott et al, "Defined Medium for Growth of *Hemophilus Influenzae*", *J. Bact.*, 101:513–516 (1970).

The above described novel free toxoid and whole bacterin-toxoid may be employed separately in vaccine compositions for induction of an antitoxin response that will prevent the pathological changes characteristic of atrophic rhinitis caused by toxigenic *P. multocida*. In a vaccine composition, an immunogenic amount of the free toxoid or the bacterin-toxoid is desirably mixed with suitable conventional vaccine adjuvants and physiologic vehicles, for injection into mammals, especially swine.

A more preferred vaccine composition is provided by a synergistic combination of the free toxoid and the whole bacterin-toxoid described above. The combination vaccine of this invention combines the whole bacterin-toxoid with the soluble toxoid, both vaccine components prepared as described above. No other toxoids or vaccines are prepared in this manner. Such a combination vaccine is prepared by mixing an immunogenic amount of free toxoid and an immunogenic amount of bacterin-toxoid with suitable adjuvants and physiologic vehicles for injection into mammals. Preferred adjuvants include amphigen and aluminum hydroxide gel.

In vaccination experiments with animals, as reported below in Examples 8 and 10, these two vaccine components have been found to act synergistically in a single vaccine preparation. The "combination vaccine" produces in the vaccinated animal a surprisingly greater effect than that expected by simply adding the effects of each toxoid component administered separately. This combination vaccine stimulates a remarkable production of antitoxin in tested animals. This combined effect can also be generated by sequentially administering the bacterin-toxoid vaccine, followed by an injection of the soluble toxoid vaccine.

While not wishing to be bound by theory, it is presently believed that the bacterin-toxoid vaccine primes the animals, particularly immunologically naive animals incapable of responding to soluble toxoid. A second dose of the bacterin-bound toxoid induces a moderate secondary response. Once primed by the toxoid-rich cells of the bacterin-toxoid, however, the animals are very responsive to the soluble free toxoid. Just as the particulate toxoid is a superior priming agent, the soluble toxoid has been observed to be a superior booster.

Still other preferred vaccine compositions of this invention result from combining the free toxoid and/or the bacterin-toxoid of this invention with other vaccinal agents. An illustrative example is a vaccine composition formed by the combination of a whole cell *B. bronchiseptica* bacterin with the *P. multocida* bacterin-toxoid. Alternatively, the *P. multocida* bacterin-toxoid is illustrated in further combination with *E. rhusiopathiae*. Other possible vaccinal agents which may be combined with the vaccine components of this invention include, without limitation, *Escherichia coli, Streptococcus suis, Mycoplasma byopneumoniae, Actinobacillus pleuropneumoniae, Clostridium perfringens* types C and D toxoids, Pseudorabies Virus Vaccine (modified live virus and/or killed virus), Rotavirus Vaccine (modified live virus), Coronavirus Vaccine (modified live virus).

Vaccines of the invention may be prepared as pharmaceutical compositions containing an effective immunogenic amount of the free toxoid and/or the whole bacterin-toxoid, as active ingredients in a nontoxic and sterile pharmaceutically acceptable carrier. A preferred embodiment of the vaccine of the invention is composed of an aqueous suspension or solution containing the free toxoid and/or bacterin-toxoid, preferably buffered at physiological pH, in a form ready for injection.

Alternatively or additionally, the free toxoid and/or bacterin-toxoid can be admixed or adsorbed with a conventional adjuvant. The adjuvant is used as a non-specific irritant to attract leukocytes or enhance an immune response. Such adjuvants include, among others, amphigen, aluminum hydroxide, muramyl dipeptide, and saponins such as Quil A.

In yet another exemplary alternative, the free toxoid and/or bacterin-toxoid can be administered with another immunostimulating preparation, such as *B. bronchiseptica* or *E. rhusiopathiae* bacterins prepared by known techniques.

It is preferred that the vaccine of the invention, when in a pharmaceutical preparation, be present in unit dosage forms. For purposes of this invention, an immunogenic amount of free toxoid, when administered as the sole active ingredient is between about 16.2 and about 32.4 μg toxoid. For purposes of this invention, an immunogenic amount of toxoid-rich cells, when injected as the sole active ingredient, is 1 ml of optical density (O.D.) between 1 and 3, as measured at 625 nm in a Spectronic 20 spectrophotometer.

In a vaccine composition containing both components, the same immunogenic amounts may be employed. Alternatively, due to the synergy of the components when combined, the immunogenic amount of the free toxoid may be reduced to about 6.5 to 8.1 micrograms.

These immunogenic amounts of the free toxoid may also be defined in terms of relative toxoid units ("RU"). The value of RU was determined empirically based on an estimate of the amount of toxoid which, when inoculated into mice, would elicit an immune response that protected mice against the lethal effects of intraperitoneal inoculation of approximately 30 $LD_{50}$ of purified toxin. In this system, an antigen extinction study was performed and a $PD_{50}$ determined. A $PD_{50}$, which is a calculated value, is defined as the amount of toxoid required to protect 50 percent of the mice from challenge with a defined amount of toxin, in this instance, 30 $LD_{50}$ of purified toxin. Thus one RU is approximately equal to one mouse $PD_{50}$.

Other appropriate therapeutically effective doses can be determined readily by those of skill in the art based on the above immunogenic amounts, the condition being treated and the physiological characteristics of the animal. Accordingly, a pharmaceutical preparation provides a unit dosage of between 0.5 to 3 mls of a sterile preparation of an immunogenic amount of the active ingredients, whether the active ingredient is the free toxoid only, the cell-bound toxoid only, or a combination thereof. In the presence of additional active agents, these unit dosages can be readily adjusted by those of skill in the art. More desirably, a pharmaceutical preparation contains between 80 and 150 RU per dose of free toxoid. Another preparation desirably contains toxin-rich cells with an OD between 1 and 3.

A desirable dosage regimen involves administration of two doses of desired vaccine composition, where the antigenic content of each fraction is desirably as stated above. The mode of administration of the vaccines of the invention may be any suitable route which delivers the vaccine to the host. However, the vaccine is preferably administered subcutaneously or by intramuscular injection. Other modes of administration may also be employed, where desired, such as intradermally or intravenously.

Present investigations with swine employ intramuscular injection of two doses of vaccine administered to the subject animal at least two weeks apart. These studies have shown that, for each of the above described vaccine compositions, a primary immunization of newborn animals is desirably initiated at about one week of age with a booster dose at weaning age. For primary immunization of pregnant dams, two doses are recommended with the last dose administered two weeks before farrowing. A booster dose is recommended prior to each subsequent farrowing. Semi-annual revaccination is recommended for boars.

It will be understood, however, that the specific dose level for any particular patient will depend upon a variety of factors including the age, general health, sex, and diet of the patient; the species of the patient; the time of administration; the route of administration; synergistic effects with any other drugs being administered; and the degree of protection being sought. Of course, the administration can be repeated at suitable intervals if necessary or desirable.

The specific mechanism of protection induced by the vaccine compositions of the present invention is the induction of toxin-neutralizing antibody (antitoxin) in vaccinated animals, as indicated by the in vivo animal tests described below.

The examples which follow illustrate preferred methods for preparing the free soluble toxoid and bacterin-toxoid of the invention and for preparing and testing a variety of vaccines containing these novel components. These examples are illustrative only and do not limit the scope of the present invention.

EXAMPLE 1—PREPARING PASTEURELLA MULTOCIDA TOXOID

A. Culturing the *P. multocida*

*P. multocida* type D (strain 8) [Dr. Ross Cowart, University of Illinois, Urbana, Ill.] is subcultured in a modified chemically defined synthetic medium for one day. The medium is described by Herriott et al, *J. Bact.*, 101:513–516 (1970).

The pH of the assembled medium is adjusted to 7.3±0.2 with sterile NaOH. Cells from this culture are transferred to fresh synthetic medium and this culture, when grown, is combined with a cryopreservative and stored at −70° C. Production cultures are grown to harvest during incubation at approximately 36°±1° C. for between 3 and 24 hours following inoculation. The dissolved oxygen content of the culture is maintained by aeration with sterile air and by agitation. Sterile antifoam solution is used to control foam. The pH of the culture is maintained at 7.3±0.2.

At the end of the growth cycle, *P. multocida* cultures are examined and cell density is determined by absorbance at 650 nm. Agitation is then decreased, and aeration and pH control are discontinued.

The toxin content of the lysate is measured by mouse lethality ($LD_{50}$) and by the Enzyme-linked Immunosorbent Assay (ELISA) described below in Example 4.

B. Pre-detoxification treatment

Following growth of the organism, sterile merthiolate is added to the culture in an amount less than or equal to 0.01 percent weight per volume. Culture fluids may be aseptically transferred through closed connections to a sterile closed container. The container is connected through closed fittings to an apparatus used to physically lyse cells and release cellular contents, e.g., a "GAULIN" model 15M laboratory homogenizer.

Bacterial cells in the culture fluid are lysed by continuous passage through the pressure chamber of the homogenizer. This subjects the cells to an immediate pressure drop from between an initial pressure of between 2000 and 5000 psi to ambient pressure of 15 psi. The lysed cells are aseptically deposited into another closed container.

The lysate is clarified by sequential steps of centrifugation and/or microporous filtration. Clarified solutions may be concentrated before or after filter sterilization. Ethylenediaminetetraacetic acid (EDTA), in an amount up to a final concentration of 5 mM, and glycerol, in an amount up to a final concentration of 1.0% (vol/vol), are added before concentrating and filter-sterilizing, to prevent aggregation of the concentrated proteins.

C. Detoxification

Sterile 5N NaOH is slowly and aseptically added to sterile toxin to increase the pH to approximately 10.55±0.10 pH units. At this pH, the detoxification occurs as the mixture is allowed to stir slowly at approximately 15°±1° C. for between 15 and 24 hours. The pH is not adjusted thereafter until detoxification is complete or aliquots are taken to measure residual toxicity. Sterile 5 N HCl is then slowly and aseptically added to adjust the pH to 6.80±0.20 pH units.

At two-hour intervals beginning 16 hours after the pH is adjusted to 10.55, an aliquot is taken. Residual toxicity of each aliquot is measured and expressed in mouse $LD_{50}$'s per mL. A preparation with an initial value of nearly 10,000 $LD_{50}$'s per mL is usually detoxified 18 hours after adjusting the pH to 10.55, without appreciable decrease in assayable antigen content. Thereafter the pH is adjusted to 6.80±0.1 unit with 5N HCl. The toxoid is then stored at 2° to 7° C. until combined with other components and assembled into vaccine compositions. If the injection of mice shows any residual toxicity, the pH of the preparation is again raised to 10.55, and the temperature to 15° C. After several hours, depending on the degree of toxicity detected, the preparation is neutralized, cooled, stored, and tested once more.

EXAMPLE 2—VACCINE FORMULATION

An illustrative toxoid vaccine formulation according to the invention was made by preparing the soluble free toxoid as described above in Example 1.

The buffer used to prepare the vaccine compositions is sterile saline at a neutral pH. Sterile aluminum hydroxide gel is used as adjuvant and added at a level sufficient to adsorb toxoid, generally 12%±1% (vol/vol). The vaccine compositions are prepared by thoroughly mixing, then dispensing the indicated amount of toxoid and aluminum hydroxide gel into a 500 ml beaker. Sterile saline is then added. This mixture is stirred and stored at 4° C. Dosage amounts of 2 ml/dose are desirable, which provides about 450 relative dosage units per dose.

Table I illustrates the formulation of two free-toxoid vaccines according to the invention.

TABLE I

| Experimental Lot | Component | Total Volume |
|---|---|---|
| A | Toxoid Concentrate | 150.0 ml |
|   | Aluminum Hydroxide Gel | 36.0 ml |
|   | Sterile Saline | 114.0 ml |
|   | Total | 300.0 ml |
| B | Toxoid Concentrate | 235.0 ml |
|   | Aluminum Hydroxide Gel | 41.0 ml |
|   | Sterile Saline | 304.0 ml |
|   | Total | 580.0 ml |

These free-toxoid vaccine formulations are useful as an aid in prevention of atrophic rhinitis in swine caused by *P. multocida* infections. An exemplary test of the free toxoid vaccine is performed by injecting the formulations into swine (pigs and dams) as described below.

EXAMPLE 3—VACCINATION EXPERIMENTS

Using the formulations of Example 2, vaccinations were administered intramuscularly to pigs and dams selected at random according to the following protocols. In each test after vaccination the animals were challenged with purified toxin at a dose known to consistently induce clinical signs of atrophic rhinitis in pigs. Toxicity of DNT was evaluated in mice before and after challenge. The total dose of toxin each pig received was 8.4 μg, or 50 mouse $LD_{50}$. Toxin was administered in three equal doses over a three day period beginning approximately two weeks following vaccination.

Results of the challenge were evaluated approximately 28 days following the first dose of toxin. The percent weight gain was calculated by the number of pounds gained in the 28 days following challenge divided by the weight, in pounds, at challenge. Nasal turbinate atrophy was evaluated by cross-section of the snout at the first premolar tooth as follows: score 0, normal; score 1, minimal atrophy; score 2, moderate atrophy; score 3, substantial atrophy; score 4, near complete atrophy; and score 5, complete atrophy.

Protocol I: Four gilts were vaccinated with a 2 ml dose of *P. multocida* free toxoid (A), described above in Example 2. Two gilts failed to farrow because of an infection of porcine parvovirus and were removed from the facility as soon as disease was evident. Pigs born of the two remaining gilts were vaccinated at 13 days of age (gilt 637, 7 pigs) and 9 days of age (gilt 638, 4 pigs) with a 2 ml dose of *P. multocida* free toxoid (B), described in Example 2. Second vaccinations were administered to all pigs two weeks later. Pigs were challenged with a dose of toxin two weeks following the second vaccination. Gilts from the same herd with farrowing dates similar to vaccinated gilts provided contemporary unvaccinated control pigs.

Following challenge, vaccinated and unvaccinated control pigs were commingled until they were slaughtered for final scoring. Table II illustrates the effects of challenge on pigs which were farrowed from dams vaccinated with two doses of vaccine A, and which were themselves vaccinated (VX) with two doses of free toxoid vaccine B, compared to unvaccinated (NonVX) animals. These results show significantly lower snout scores and significantly better weight gains in the vaccinated group.

TABLE II

| Group | No. | Weight at Challenge | Weight at Slaughter | Weight Gain (lb) | Weight Gain % | Mean Snout Score |
|---|---|---|---|---|---|---|
| VX | 10 | 26.20 | 39.60 | 13.40 | 54.27 | 1.00 |
| Non-VX | 8 | 22.88 | 31.56 | 8.69 | 35.30 | 2.34 |

Protocol II: Four gilts were vaccinated with a 2 ml dose of vaccine A. One gilt failed to farrow because of an infection of porcine parvovirus and was removed from the facility as soon as disease was evident. Pigs from remaining gilts were challenged with toxin as follows: 9 pigs from one gilt at 10 days old; 2 pigs from a second gilt at 12 days old; and 6 pigs from a third gilt at 4 days old. Gilts from the same herd with farrowing dates similar to vaccinated gilts provided contemporary unvaccinated control pigs.

Vaccinated and unvaccinated control pigs were challenged prior to weaning and thereafter commingled until slaughtered for final scoring. Table III summarizes the effects of challenge on pigs farrowed by dams which received two doses of vaccine A. The data are presented (a) independently of litter, and (b) by litter averages.

These results show significantly lower snout scores and significantly better weight gains in the vaccinated group. These observations indicate that two doses of vaccine A given to dams induced the production of antitoxin that was passively transferred to otherwise susceptible pigs. Furthermore, the duration of passive protection was at least 10 to 12 days.

TABLE III

| Group | No. | Weight at Challenge | Weight at Slaughter | Weight Gain (lb) | Weight Gain % | Mean Snout Score |
|---|---|---|---|---|---|---|
| (a) | | | | | | |
| VX | 15 | 6.87 | 21.00 | 14.13 | 205.83 | 3.02 |
| Non-VX | 5 | 8.20 | 16.40 | 8.20 | 100.00 | 3.70 |
| (b) | | | | | | |
| VX | | | | | | |
| Gilt 629 | 7 | 8.71 | 21.50 | 12.79 | 147.09 | 3.68 |
| Gilt 639 | 2 | 8.00 | 29.25 | 21.25 | 268.65 | 2.38 |
| Gilt 633 | 6 | 4.33 | 17.67 | 13.33 | 310.28 | 2.46 |
| Gilt Avg | | 7.02 | 22.81 | 15.79 | 242.01 | 2.84 |
| Non-VX | 5 | 8.20 | 16.40 | 8.20 | 100.00 | 3.70 |

EXAMPLE 4—ELISA TO QUANTIFY ANTIBODY

Pig sera and colostrum samples from the experiments of Example 3 were tested for antibodies against the toxin by a kinetic ELISA. Briefly, purified toxin (250 ng/well) in 0.1M sodium borate, pH 9.1, was adsorbed to flat-bottom 96 well Nunc microtiter plates overnight at 4° C. Plates were then blocked at 37° C. for 30 minutes with 10% nonfat dried milk in PBS with 0.05% Tween-20 (blocking buffer). Blocking buffer was rinsed from the plates with two PBS/0.05% Tween-20 (PBS/Tween) rinses, followed by a PBS rinse. Sera were diluted 1:100 in blocking buffer, and 50 μl samples were added to each of four wells. Plates were incubated for 60 minutes at 37° C., and then rinsed as above.

Goat-anti swine IgG (heavy and light chain specific)-horseradish peroxidase [Kirkegaard and Perry Laboratories, Gaithersburg, Md.] was diluted 1:500 in blocking buffer, and added (50 μl) to each well. Following a 60 minute incubation at 37° C., plates were rinsed as above. ABTS substrate (2,2'-axino-di-3-ethylbenzthiazoline sulfonate) [Kirkegaard and Perry] was added, and plates were read immediately on a Vmax ELISA reader at 405 nm [Molecular Devices Corporation, Palo Alto, Calif.]. Each well was read eight times during a one-minute interval, and the rate of the enzymatic reaction was calculated.

Rates were calculated as the change in milli units of optical density (mOD) per minute. Thus a reading of 100 mOD per minute would be equal to an OD of 1.0 in 10 minutes. Values were then corrected for the amount of serum used per well and reported as mOD/min/ml of serum. For instance, if 50 μl of serum produced a reading of 100 mOD per minute, the reported value would be 2,000 mOD units per minute per ml.

The following controls were included on each ELISA plate. (1) Serum control: each diluted pig serum was placed in a well that did not contain antigen, then exposed to all subsequent reagents to check for non-specific adsorption to the plate. At the dilution of pig sera (1:100) used, no color greater than that obtained in the negative serum control was seen. (2) Negative pig serum control: each plate included three wells of a known negative pig serum diluted 1:100 in blocking buffer. (3) Positive pig serum controls: serum containing specific antibodies to the toxin was diluted in negative pig serum to obtain sera containing high, moderate, and low concentrations of specific antibody. These three sera were diluted 1:100 in blocking buffer and placed in triplicate on each plate. Background, or non-specific reactivity, was determined in wells that contained all reagents except pig serum.

Table IV below summarizes the ELISA titers of the dams and pigs vaccinated with toxoid vaccines A and B, respectively, according to Protocol II (Example 4). The table gives the geometric mean titers of sera taken before the first and second dam vaccinations, of the colostrum, and of sera taken before the first and second pig vaccinations, challenge, and slaughter, as compared to unvaccinated controls (Non-Vx).

TABLE IV

| | Geometric Mean ELISA Titers | | | | | | |
|---|---|---|---|---|---|---|---|
| Group | 1st Dam Vx | 2nd Dam Vx | Colostrum | 1st Pig Vx | 2nd Pig Vx | Challenge | Slaughter |
| VX | 21.71 | 0 | 173.00 | 0.99 | 1.73 | 109.03 | 139.07 |
| Non VX | 25.35 | 12.34 | 83.38 | 1.45 | 1.72 | .38 | 8.64 |

These results indicate that two doses of vaccine A given to dams, followed by two doses of vaccine B given to their pigs, induced immunity to the toxin in otherwise susceptible pigs.

From the same study (Protocol II, Example 4) Table V summarizes the ELISA titers of vaccinated (vaccine A) and unvaccinated dams and their unvaccinated pigs.

TABLE V

| | Geometric Mean ELISA Titers | | | | |
|---|---|---|---|---|---|
| A: Group | 1st Dam Vx | 2nd Dam Vx | Colostrum | Challenge | Slaughter |
| Vx | 28.19 | .76 | 104.31 | 7.98 | 22.53 |

TABLE V-continued

| | | | | | |
|---|---|---|---|---|---|
| Non-Vx | 27.56 | 15.53 | 80.60 | .19 | .75 |

Individual ELISA titers

| B: Group | 1st Dam Vx | 2nd Dam Vx | Geometric mean titers of litters at: Colostrum | Challenge | Slaughter |
|---|---|---|---|---|---|
| Vaccinated | | | | | |
| Gilt 629 | 21.80 | 5.80 | 70.60 | 1.66 | 29.15 |
| Gilt 639 | 29.20 | — | 18.60 | 26.07 | 25.39 |
| Gilt 633 | 35.20 | — | 154.10 | 36.43 | 16.03 |
| Average | 27.73 | 1.93 | 81.10 | 21.39 | 23.03 |
| Unvaccinated | | | | | |
| Gilt 636 | 23.40 | 10.80 | 66.80 | — | 12.40 |
| Gilt 631 | 30.60 | 11.90 | 135.90 | — | 0.20 |
| Gilt 626 | 19.80 | 17.60 | 76.70 | — | 9.40 |
| Gilt 635 | 40.60 | 20.40 | — | — | — |
| Gilt 632 | 27.60 | 19.60 | 60.60 | 4.60 | — |
| Average | 28.40 | 16.06 | 68.00 | 0.92 | 4.4 |

Table VI shows a summary of challenge-of-immunity studies for dam and pigs vaccinated with various doses (in relative toxoid units, RU) of free toxoid preparations.

TABLE VI

| RU Administered to: | | | Significant Protection against | |
|---|---|---|---|---|
| Dams | Pigs | No. | Weight Loss | Turbinate atrophy |
| 876 + 32 | 307 + 70 | 10 | Yes | Yes |
| 876 + 32 | 0 | 15 | Yes | Yes |
| 391 + 52 | 0 | 10 | No | No |
| 0 | 391 + 52 | 9 | No | No |

The data shows significant protection of pigs farrowed by dams vaccinated with two doses of a vaccine containing 876±32 RU of free toxoid. In pigs or pregnant gilts, two doses of experimental lots containing between 300 and 400 RU/dose, did not appear to induce protection.

EXAMPLE 5—PREPARING A BACTERIN-TOXOID VACCINE COMPOSITION

An embodiment of this composition includes a bacterin-toxoid of *P. multocida* in which the toxoid has been stabilized within the bacterial cell.

A culture of *P. multocida*, type D, strain 8, is grown in the following medium: Tryptic Soy Broth without Dextrose (Difco) 30 g; Yeast extract (Difco) 5 g; Dextrose 4 g; Deionized water to 1 liter; pH of approximately 7; sterilized by autoclaving at 121° C.

The culture is aerated with agitation to maintain the dissolved oxygen concentration at approximately 35% of saturation. The temperature is maintained at 37° C., and the pH at 7 by the addition of 10N NaOH solution as needed. Towards the end of exponential growth, aeration is discontinued and the culture is inactivated by the addition of formaldehyde solution (USP) to a final concentration of 0.5% v/v. The culture is then held at 37° C. for four days. Other inactivating agents, such as beta-propriolactone, glutaraldehyde, and binary ethyleneamine can be used in place of formaldehyde.

A sample is withdrawn to test whether inactivation is complete by administering the sample to guinea pigs. Guinea pigs should be alive and healthy at 7 days after subcutaneous injection with 4 ml volumes of the culture. At this point the toxin within the cells is completely converted to toxoid, which is safe, very stable and capable of inducing the production of neutralizing antitoxins upon injection into animals.

The inactivated culture is centrifuged. The sedimented bacteria are dispensed in sufficient supernatant fluid to make a suspension with an OD (optical density at 625 nm, as determined in a Spectronic 20 spectrophotometer) of 4.2. The suspension is then adsorbed with $Ai(OH)_3$ gel, 25% v/v, thimerosol (0.01% w/v) is added as a preservative, and the pH is adjusted to 6.5±0.2.

This *P. multocida* bacterin-toxoid may be used in vaccines as the sole vaccine component.

Alternatively, the bacterin toxoid may be employed in vaccine compositions with other vaccine components. For example, the suspension of adsorbed *P. multocida* is mixed with equal volumes of similarly adsorbed and preserved cultures of *Bordetella bronchiseptica* and *Erysipelothrix rhusiopathiae* to make a bacterin-toxoid vaccine, referred to as Atrobac 3 (Beecham Laboratories), which has a dose volume of 2 ml. Whether the bacterin-toxoid is used alone or in combination, saponin (0.5 mg/ml) may be added as adjuvant.

EXAMPLE 6—A COMBINATION VACCINE

Combination vaccines may contain the bacterin toxoid of Example 5, and/or the soluble toxoid of Example 1 with optional components, such as other inactivated microorganisms, e.g., *B. bronchiseptica* and other strains of *P. multocida* (*P. multocida* serotype A for protection against pleuritic and pneumonic forms of pasteurellosis).

One exemplary combination vaccine employs the *P. multocida* bacterin-toxoid described in Example 5 and the *P. multocida* free toxoid described in Example 1. Another combination vaccine may include the free toxoid and bacterin toxoid of *P. multocida* type D, described above, with an inactivated whole culture of *B. bronchiseptica*.

Still another efficacious vaccine composition against infection by *P. multocida* can be prepared by combining the bacterin-toxoid vaccine composition, Atrobac 3, described above in Example 5, and the soluble, free toxoid of *P. multocida* prepared as described above in Example 1.

One exemplary formulation for a combination vaccine consists of the following components:

| Component | Vol/ds (ml) | Vol (ml) |
|---|---|---|
| Atrobac 3 | 2.000 | 250.00 |
| Free toxoid (650 U/ml) | 0.242 | 30.25 |
| oil/lethicin | 0.100 | 12.50 |
| Tween 80 | 0.056 | 7.00 |
| Span 80 | 0.024 | 3.00 |
| TOTALS | 3.000 | 375.00 |

For emulsification, these components were combined and emulsified, as a single batch, for 2 minutes. For production scale, it is anticipated that metered in-line rather than batch combination is desirable.

Other ingredients may be added to, or may replace existing ingredients in, the specific formulation above. For example, aluminum hydroxide gel may be employed as an adjuvant in place of oil/lethicin.

EXAMPLE 7—A COMBINATION VACCINE

Another combination vaccine was prepared as follows: *B. bronchiseptica*, Strain 2-9 NADC [National Animal Disease Center, Ames, Iowa] was subcultured six times. *P. multocida* type A strain 169 was cultured in a manner similar to that described for strain 8 in Example 1. For example, at the end of their respective growth periods, cultures of *B. bronchiseptica* and *P. multocida* type A strain 169 are inactivated by the addition of beta-propiolactone (BPL). A second addition of BPL is made 2 to 18 hours following the first. The final concentration of BPL does not exceed 1:500 (0.2%). Each culture is incubated at less than 20° C. with constant agitation for at least 12 hours.

For inactivated cultures of *B. bronchiseptica* and *E. multocida* type A strain 169, sterile mineral oil [Drakeoil] containing 3.3% to 40% by weight of lecithin [Central Soya] is added as adjuvant. In the final product, the concentration of the oil fraction is approximately 5% by volume. Tween 80 is added to a final concentration of between 0.7 and 2.8%. An emulsifier is added to a final concentration of about 0.3 to 1.2% (e.g., Span 80). A selected paraben, e.g. methyl p-hydroxyl-benzoate, propyl p-hydroxylbenzoate, or butyl p-hydroxylbenzoate, may be added as an additional preservative.

The *P. multocida* free toxoid is mixed with sterile aluminum hydroxide gel (equivalent to 2% $Al_2O_3$) as adjuvant. In the final product the concentration of aluminum hydroxide gel is 12% by volume.

Concentration is performed by ultrafiltration under aseptic conditions.

In an exemplary combination vaccine, the *B. bronchiseptica* fraction contains at least 1500 nephelometric units per vaccine dose. The nephelometric units are based on the value measured at the time of harvest. The *E. multocida* type A strain 169 fraction contains at least 3.4 absorbance units per dose. The absorbency units are based on the value measured at the time of inactivation. The *P. multocida* free-toxoid fraction contains at least 450 relative toxoid units per 2.0 ml dose. Relative toxoid units are measured prior to final product assembly.

One or more complete or partial bulk lots of each fraction are combined with adjuvant and saline diluent to obtain the standard antigen concentration.

These fractions are formulated prior to final assembly by combining the *B. bronchiseptica* and *P. multocida* type A strain 169 components (Fraction I), preparing the free toxoid formulation (Fraction II), and combining Fractions I and II (Vaccine) in the proportions shown in Table VII below.

TABLE VII

| Component | Vol/2.0 ml dose (ml) | Total Vol (ml) |
|---|---|---|
| FRACTION I: | | |
| *B. bronchiseptica* | 0.250 | 6,250 |
| *P. multocida* type A 169 | 0.500 | 12,500 |
| Oil/Lethicin | 0.100 | 2,500 |
| Saline | 0.150 | 3,750 |
| Totals | 1.000 | 25,000 |
| FRACTION II: | | |
| *P. multocida* Toxoid | 0.300 | 7,500 |
| Al(OH)$_3$ gel | 0.240 | 6,000 |
| Saline | 0.460 | 11,500 |
| Totals | 1.000 | 25,000 |

TABLE VII-continued

| Component | Vol/2.0 ml dose (ml) | Total Vol (ml) |
|---|---|---|
| VACCINE: | | |
| Fraction I | 1.000 | 25,000 |
| Fraction II | 1.000 | 25,000 |
| Totals | 2.000 | 50,000 |

EXAMPLE 8—VACCINE TESTS IN ANIMALS

The vaccine compositions of Examples 2, 5, 6 and 7 are useful in the prevention of atrophic rhinitis and pneumonia in swine caused by *B. bronchiseptica* and/or *P. multocida*. During the vaccine tests, it was surprisingly observed in the evaluation of the antibody response in swine, that combining the *P. multocida* bacterin-toxoid and free toxoid had more than an additive effect on the induction of antitoxin, compared to use of the bacterin-toxoid alone or the free toxoid alone.

In one experiment, groups of pigs were vaccinated with Atrobac 3, which contains the *P. multocida* bacterin-toxoid and preserved cultures of *B. bronchiseptica* and *E. rhusiopelothrix* (Example 5), or with the free soluble *P. multocida* toxoid of Example 1 only, or with a combination of bacterin-toxoid and soluble toxoid as described in Example 6. Table VIII demonstrates antibody response to vaccination with free toxoid alone, with bacterin-toxoid alone and with a combination of these two vaccine components. The ELISA titers indicate a synergistic effect of this combination vaccine. This combination vaccine composition is believed to induce the best immunity in swine.

The post vaccination sera were also assayed for neutralizing antitoxin, the actual protective antibody, by the method of Roberts and Swearingin, *Am. J. Vet. Res.*, 49:2168 (1988). The antitoxin values show a strong synergy of the free and cell-bound toxoids (Table VIII).

Table IX demonstrates the results of another experiment wherein a vaccine containing whole cell inactivated cultures of *P. multocida* (PmD), soluble toxoid and *B. bronchiseptica* inactivated whole cells (Bb), was used in guinea pigs and serum antibody levels measured by the EBL tissue culture assay [J.M. Rutter et al, *Veterinary Record*, 114:393–396 (1984)]. In this experiment the combination vaccine dosage unit is 2 ml/dose. In this experiment 600 RU toxoid failed to induce an appreciable anti-toxin response. In contrast, 600 RU toxoid combined with inactivated cultures of *P. multocida* (PmD) induced an anti-toxin response level of 128. This demonstration serves as yet another example of immunologic synergy for soluble toxoid and inactivated cultures of toxigenic *P. multocida*.

TABLE VIII

| No. Pigs | Bacterin Toxoid (ml) | Free Toxoid (RU) | Adjuvant | Serum Antibody Levels PRE Vx | Serum Antibody Levels POST Vx | Neutralizing Antitoxin units/ml POST Vx |
|---|---|---|---|---|---|---|
| 8 | 0 ml | 200 | Al$_2$OH$_3$ | <10 | 13 | <1 |
| 8 | 0 ml | 200 | Amphigen-Al$_2$OH$_3$ | <10 | 16 | <1 |
| 8 | 2 ml | 0 | Al$_2$OH$_3$ | <10 | 93 | 20 |

TABLE VIII-continued

| No. Pigs | Bacterin Toxoid (ml) | Free Toxoid (RU) | Adjuvant | Serum Antibody Levels PRE Vx | Serum Antibody Levels POST Vx | Neutralizing Antitoxin units/ml POST Vx |
|---|---|---|---|---|---|---|
| 8 | 2 ml | 0 | Amphigen-Al$_2$OH$_3$ | <10 | 46 | 20 |
| 8 | 2 ml | 120 | Al$_2$OH$_3$ | <10 | 252 | 40 |
| 8 | 2 ml | 120 | Amphigen-Al$_2$OH$_3$ | <10 | 302 | 80 |

TABLE IX

| Bacterin-Toxoid | Free Toxoid (RU) | Dose Fraction | Adjuvant | Serum Antibody Levels PRE-Vx | Serum Antibody Levels POST-Vx |
|---|---|---|---|---|---|
| Bb + PmD | 600 | 1/25 | Amphigen-Al$_2$OH$_3$ | <2 | 128 |
| Bb + PmD | 300 | 1/25 | Amphigen-Al$_2$OH$_3$ | <2 | 4 |
| Bb + PmD | 0 | 1/25 | Amphigen-Al$_2$OH$_3$ | <2 | <2 |
| Bb | 600 | 1/25 | Amphigen-Al$_2$OH$_3$ | <2 | 4 |
| Bb | 300 | 1/25 | Amphigen-Al$_2$OH$_3$ | <2 | <2 |

EXAMPLE 9—A COMBINATION VACCINE

A further embodiment of the vaccine compositions of this invention includes a combination vaccine containing a *B. bronchiseptica* bacterin, a *P. multocida* toxoid of Example 1, a *P. multocida* type A strain 169 bacterin described in Example 7, and an *E. rhusiopathiae* bacterin. This vaccine is useful for the vaccination of healthy swine as an aid in prevention of atrophic rhinitis, erysipelas and pneumonia caused by *B. bronchiseptica*, *Erysipelothrix rhusiopathiae* and *P. multocida*.

Cultures of *B. bronchiseptica* and *E. multocida* type A strain 169 are inactivated and individually formulated into fractions as described in the above example.

Cultures of *E. rhusiopathiae* strain SE-9 [Dellen Labs, Omaha, Nebr.] are inactivated by the addition of formaldehyde solution (37 percent) to a final concentration of 0.35 to 0.45 percent. The *E. rhusiopathiae* fraction is formulated in aluminum hydroxide gel as described for the free-toxoid fraction.

The free toxoid is prepared and formulated as described above in Examples 1 and 2.

Concentration is performed by ultrafiltration under aseptic conditions.

Each fraction is combined with adjuvant and saline diluent to obtain the standard antigen concentration. These fractions are formulated prior to final assembly by combining the *B. bronchiseptica* and *P. multocida* type A strain 169 components (Fraction III), preparing the free toxoid and *E. rhusiopathiae* components (Fraction IV) and combining Fractions III and IV (Vaccine) in the proportions shown in the Table X below.

TABLE X

| Component | Vol/3.0 ml dose (ml) | Total Vol (ml) |
|---|---|---|
| FRACTION III: | | |
| *B. bronchisentica* | 0.250 | 6,250 |
| *P. multocida* type A 169 | 0.500 | 12,500 |
| Oil/Lethicin | 0.100 | 2,500 |
| Saline | 0.150 | 3,750 |
| Totals | 1.000 | 25,000 |
| FRACTION IV: | | |
| *E. rhusiopathiae* | 0.500 | 12,500 |
| *P. multocida* 8 Toxoid | 0.300 | 7,500 |
| aluminum hydroxide gel | 0.600 | 15,000 |
| Saline | 0.600 | 15,000 |
| Totals | 2.000 | 50,000 |
| VACCINE: | | |
| Fraction III | 1.000 | 25,000 |
| Fraction IV | 2.000 | 50,000 |
| Totals | 3.000 | 75,000 |

Each dose of vaccine contains at least 1500 nephelometric units of *B. bronchiseptica*, at least 3.0 absorbency units of *E. rhusiopathiae*, at least 3.4 absorbance units at 650 nm of *E. multocida* type A strain 169, and at least 450 relative units of *P. multocida* toxoid. The absorbency units are based on the value measured at the time of harvest.

EXAMPLE 10—VACCINATION EFFICACY EXPERIMENTS

Five experimental vaccines according to the present invention were evaluated for efficacy in animal studies using pathogenic challenge of vaccinated and unvaccinated animals. The experimental vaccines are formulated essentially as described above and include the following active components as set out in Table XI below:

TABLE XI

| VX | *B. bronchiseptica* | *P. multocida* Strain 169 | Toxoid | *E. rhusioipathiae* |
|---|---|---|---|---|
| C | 170 mls | 425 mls | 646 mls | 0 |
| D | 170 | 0 | 646 | 0 |
| E | 220 | 505 | 260 | 0 |
| F | 300 | 689 | 355 | 1035 |
| G | 200 | 591 | 250 | 350 |

I. *P. multocida* type A Challenge

One experiment was conducted as follows: On day 1 and day 14, ten pigs were vaccinated with a 2 ml dose of Vaccine C and ten pigs with a 2 ml dose of Vaccine D. Two weeks after the second inoculation, these pigs and ten contemporary unvaccinated controls were infected with *P. multocida* strain 169. Disease severity was quantified by a clinical score at death or two weeks after infection (Table XII).

TABLE XII

| VX | No. | Dead/Total | Clinical Scores Mean ± S.D. | Signif. |
|---|---|---|---|---|
| C | 10 | 1/10 | 4.0 ± 2.75 | p < .0025 |
| D | 10 | 5/10 | 9.0 ± 1.41 | none |
| NonVx | 10 | 5/10 | 8.4 ± 2.31 | CONTROL |

Table XIII summarizes the agglutinin responses [geometric mean titer (GMT)] of the three groups to *P. multocida*, at first and second vaccinations, at challenge, and at death or slaughter.

TABLE XIII

| | AGGLUTININ TITERS (GM) | | | |
|---|---|---|---|---|
| VX | 1st Vaccine | 2nd Vaccine | At Challenge | At Death or Slaughter |
| C | <4 | 16 | 138 | 939 |
| D | <4 | <4 | <4 | 36 |
| NonVX | <4 | <4 | <4 | 128 |

Following challenge, clinical signs in susceptible pigs were consistently severe. Predominant clinical signs included death (or moribundity), lameness, and pleuritis and pericarditis with fibrinous deposits and adhesions. These signs were abundant in all pigs except those vaccinated with Vaccine C. Of the ten pigs given Vaccine C, substantial protection was evident in nine. Based on these observations, two doses of Vaccine C given to susceptible pigs induced immunity to challenge with *P. multocida* type A.

II. Toxin Challenge

Another experiment was performed as follows: On day 1 and day 15, five pregnant dams were vaccinated with Vaccine D (2 ml dose) and five with Vaccine E (2 ml dose). Farrowings occurred beginning about two weeks thereafter. Five pigs from each of the ten vaccinated dams and five pigs from unvaccinated dams were given a 2 ml dose of Vaccine E. At weaning, vaccinated pigs and unvaccinated pigs (littermates to vaccinated pigs farrowed from unvaccinated dams) were challenged with toxin. About one month thereafter, pigs were scored for clinical signs of atrophic rhinitis.

A summary of weight gains and snout scores for each group is shown in Table XIV below.

TABLE XIV

| | Group Mean Values | | | | | | |
|---|---|---|---|---|---|---|---|
| | Number | | Wt. (lbs) at: | | Wt Gain by: | | Snout |
| Group | Dams | Pigs | Chal. | Final | (lbs) | % | Score |
| 1 | 5 | 25 | 21.32 | 59.04 | 37.72 | 179.11 | 1.13 |
| 2 | 5 | 25 | 19.96 | 57.48 | 37.52 | 191.80 | 1.02 |
| 3 | 5 | 25 | **21.76 | 51.62 | 29.67 | 138.97 | 2.83 |
| | | | ***21.76 | 43.72 | 21.96 | 99.95 | |
| 4 | 5 | 10 | **21.20 | 52.43 | 31.00 | 144.91 | 2.57 |
| | | | ***21.20 | 36.70 | 21.70 | 101.44 | |
| 5 | 4 | 4 | 23.50 | 64.75 | 41.25 | 176.58 | 0.44 |

Group 1: Vaccinated: Dams - vaccine D; Pigs - vaccine E
Group 2: Vaccinated: Dams - vaccine E; Pigs - vaccine E
Group 3: Vaccinated: Dams - None; Pigs - vaccine E
Group 4: Unvaccinated: Dams and Pigs
Group 5: Sentinel
*Pigs in groups 3, 4, and 5 were farrowed from common dams
**Values calculated using only pigs surviving challenge
***Values calculated including pigs not surviving challenge Pigs in groups 1 and 2 (Table XIII) gained 37.72 and 37.52 pounds per litter, or 179.11 and 191.80 percent, respectively. Susceptible pigs, groups 3 and 4, gained 29.67 and 31.00 pounds, or 138.97 and 144.91 percent, respectively. The difference in weight gains for susceptible pigs (groups 3 and 4, n=35) were compared to weight gains for vaccinated and protected pigs (groups 1 and 2, n=50) by student "t" test. The difference was very highly significant (p <<0.0005) showing increased weight gain for groups 1 and 2 (Table XIII). The snout scores for susceptible pigs (groups 3 and 4) were compared to those for pigs in groups 1 and 2. There was a marked decrease in the destruction of nasal turbinates in groups 1 and 2. The difference was highly significant (Student "t" test: p <0.0005). According to the analysis of weight gains and nasal turbinate scores, pigs in groups 1 and 2 were protected from challenge with toxin (Table XIV).

Serum samples were collected immediately prior to each dam and pig vaccination, from the dam at farrowing, from pigs when challenged with toxin (chal), and from pigs when signs of AR were scored (slaughter). Table XV summarizes the antibody titers of the dams and pigs in the various treatment groups. N/A means the data are not available.

TABLE XV

| Group | 1st Dam Vx | 2nd Dam Vx | Farrow | Colostrum | 1st Pig Vx | 2nd Pig Vx | Chal | Slaughter |
|---|---|---|---|---|---|---|---|---|
| 1 | | | | | | | | |
| Bb | 21.11 | 294.06 | 147.03 | 776.05 | 25.64 | 19.97 | 22.05 | 7.16 |
| PmA | 16.00 | 18.38 | 10.56 | 10.56 | <4 | 6.53 | 82.14 | 105.40 |
| PmD | 9.58 | 11.33 | 30.48 | 195.14 | 18.95 | 11.94 | 61.36 | 248.53 |
| 2 | | | | | | | | |
| Bb | 24.25 | 512.00 | 222.85 | 1552.00 | 28.65 | 17.88 | 14.72 | 18.38 |
| PmA | 16.00 | 73.52 | 73.52 | 168.90 | 32.90 | 13.93 | 65.80 | 75.59 |
| PmD | 6.13 | 9.99 | 32.36 | 245.14 | 28.56 | 16.49 | 106.02 | 272.76 |
| 3 | | | | | | | | |
| Bb | N/A | N/A | 9.19 | 42.22 | 5.90 | 7.78 | 17.67 | 14.32 |
| PmA | N/A | N/A | 8.00 | 12.13 | <4 | 8.69 | 91.77 | 100.43 |
| PmD | N/A | N/A | 7.56 | 12.48 | 5.03 | 5.06 | 5.88 | 24.60 |
| 4 | | | | | | | | |
| Bb | N/A | N/A | 9.19 | 42.22 | 5.28 | 4.67 | 4.29 | 4.88 |
| PmA | N/A | N/A | 8.00 | 12.13 | <4 | 4.30 | 5.15 | <4.00 |
| PmD | N/A | N/A | 7.56 | 12.48 | 3.04 | 3.46 | 4.34 | 3.67 |
| 5 | | | | | | | | |
| Bb | N/A | N/A | 8.00 | 38.05 | 13.45 | 8.00 | 5.66 | 4.76 |
| PmA | N/A | N/A | 8.00 | 12.13 | 11.32 | 6.73 | 5.66 | <4.00 |
| PmD | N/A | N/A | 7.56 | 12.48 | 2.73 | 4.19 | 4.40 | 1.67 |

Geometric Mean Titer (GMT) to each fraction for sera taken at or before:

For purposes of Table XV, the symbol Bb means *B. bronchiseptica*; PmA means *P. multocida* type A (strain 169) and PmD means *P. multocida* toxin. The vaccine groups are as defined in Table XIV.

These results show that two doses of Vaccine E did not induce antibody to toxin when given to pigs farrowed from unvaccinated dams. These pigs remained susceptible to challenge with toxin. In contrast, two doses of Vaccine E induced antibody to toxin in pigs farrowed from vaccinated dams. From these data, vaccination of dams and pigs with toxoid immunized pigs against the toxin of *P. multocida*.

III. Challenge with *E. rhusiopathiae*

Still an additional experiment was performed as follows: On day 1 and day 14, eight pigs each were vaccinated with vaccines F and G (see Table XI). On the same dates eight pigs were vaccinated with two doses of vaccine E. On day 1 four pigs were vaccinated with a single dose of erysipelothrix bacterin. On about day 30, pigs were challenged with virulent *E. rhusiopathiae*.

A summary of response to challenge is presented in Table XVI below.

TABLE XVI

| Vaccine | Number Normal | Total | Percent | Result |
|---|---|---|---|---|
| F | 8 | 8 | 100 | [3]Sat |
| G | 7 | 8 | 87.5 | [3]Sat |
| [1]Exp. ER | 4 | 4 | 100 | [3]Sat |
| [2]E | 2 | 8 | 25 | [4]Sat |

TABLE XVI-continued

| Vaccine | Number Normal | Total | Percent | Result |
|---|---|---|---|---|

[1]Vaccinated: single dose of an experimental *Erysipelothrix rhusiopathiae* bacterin. Pigs in this group served as a positive control.
[2]Vaccinated: 2 doses vaccine E (no erysipelothrix). Pigs in this group served as susceptible controls for challenge with virulent *E. rhusiopathiae* and for comparison of serologic response to unchallenged fractions.
[3]Satisfactory protection of vaccinated animals as defined in 9 CFR §113.04(e).
[4]Satisfactory disease in susceptible swine, e.g., unvaccinated controls as defined in same regulation.

The results in Table XVI show that at least 75% of the susceptible animals displayed clinical signs of erysipelas, validating the challenge. At least 75% of the animals vaccinated with two doses of vaccines F or G were without clinical signs of erysipelas. These results indicate that two doses of vaccines F or G provide effective protection against challenge with virulent *E. rhusiopathiae*.

At the end of the observation period, all surviving pigs were treated with penicillin for 4 to 5 days at 1,000 units per pound. Once signs of erysipelas were no longer apparent, all pigs were challenged with *P. multocida* toxin.

A summary of mean weight gains and snout scores for each group is shown in Table XVII below.

TABLE XVII

| Vaccine | Challenge Number | Wt | Final Wt | Wt Gain in: (lbs) | % | Snout Score |
|---|---|---|---|---|---|---|
| F | 8 | 52.25 | 72.13 | 19.88 | 38.04 | 1.63 |
| G | 8 | 51.50 | 78.25 | 26.75 | 52.13 | 1.31 |

TABLE XVII-continued

| Vaccine | Challenge Number | Challenge Wt | Final Wt | Wt Gain in: (lbs) | Wt Gain in: % | Snout Score |
|---|---|---|---|---|---|---|
| *Exp. ER | 4 | 43.75 | 63.75 | 20.00 | 45.75 | 2.50 |
| **E | 8 | 44.14 | 61.57 | 17.42 | 40.14 | 2.00 |

*Pigs in this group served as susceptible controls for challenge with DNT.
**Protection not expected (see Table XVI).

Based on the results in Tables XIV and XV, two doses of vaccine E (Table XI) were not predicted to induce a protective immune response to challenge with DNT. However, two doses of vaccine E were adequate to prime susceptible pigs since a secondary response to toxin was evident following toxin challenge (Table XVIII). Similarly, pigs vaccinated with the two vaccines ER and E did not respond as well as pigs farrowed and nursing from vaccinated dams (Table XV). However, all pigs vaccinated with vaccines F and G demonstrated a primary response to vaccination and a secondary response to toxin injection equal or superior to the group vaccinated with vaccine E. Further, pigs given vaccine E were very nearly protected from challenge. These data indicate a freedom from immunological interference between the fractions in experimental vaccines.

Serum samples were collected immediately prior to each vaccination, when *E. rhusiopathiae* challenge was administered (Erh Chal) when toxin challenge was given (PmD Chal), and at slaughter. A summary of the serological responses to fractions other than *E. rhusiopathiae* is presented in Table XVIII below.

TABLE XVIII

| | Geometric Mean Titer (GMT) to each fraction for sera taken at or before: | | | | |
|---|---|---|---|---|---|
| Group* | 1st Pig Vx | 2nd Pig Vx | Erh. Chal. | PmD Chal. | Slaughter |
| 6 | | | | | |
| Bb** | 5.19 | 16.00 | 47.61 | 40.03 | 26.25 |
| PmA | <4.00 | 8.72 | 256.00 | 166.00 | 172.57 |
| PmD | 1.33 | 7.63 | 26.19 | 20.10 | 468.71 |
| 7 | | | | | |
| Bb | 6.87 | 16.00 | 36.71 | 34.90 | 34.90 |
| PmA | <4.00 | 29.34 | 139.58 | 107.63 | 128.00 |
| PmD | 0.66 | 4.77 | 23.30 | 35.70 | 512.63 |
| 8 | | | | | |
| Bb | <4.00 | 4.00 | 4.00 | <4.00 | 4.00 |
| PmA | <4.00 | 42.22 | <4.00 | 8.00 | <4.00 |
| PmD | 4.96 | 4.19 | 4.75 | 5.67 | 4.21 |
| 9 | | | | | |
| Bb | 6.17 | 14.67 | 49.35 | 32.00 | 26.25 |
| PmA | 5.18 | 26.91 | 139.58 | 256.00 | 186.61 |
| PmD | 6.86 | 8.12 | 6.90 | 9.04 | 47.11 |

Group 6: Vaccinated, vaccine F (see Table XI)
Group 7: Vaccinated, vaccine G (see Table XI)
Group 8: Vaccinated, *Erysipelothrix rhusiopathiae* bacterin vaccine
Group 9: Vaccinated, vaccine E (see Table XI)

Pigs farrowed by unvaccinated dams and vaccinated with *Bordetella bronchiseptica-Pasteurella multocida* bacterintoxoid experimental Vaccine E were protected against challenge with *P. multocida* type A (strain 169). From this result it can be concluded that dam vaccination with this formulation is not required in protecting pigs against type A.

Vaccination of both dams and pigs with product formulated to contain at least 300 RU/dose of toxoid is required for the protection of pigs against challenge with toxin.

Experimental *Bordetella bronchiseptica-Erysipelothrix rhusiopathiae-Pasteurella multocida* bacterintoxoid given to susceptible pigs protected at least 75% against a valid challenge with virulent *E. rhusiopathiae*. From this result it is concluded that two doses of this bacterin-toxoid formulated as either a 3 ml dose or a 2 ml dose induced effective immunity against erysipelas.

Numerous modifications and variations of the present invention are included in the above-identified specification and are expected to be obvious to one of skill in the art. For example, use of other appropriate inactivated pathogens, other than those of *B. bronchiseptica* and *E. rhusiopathiae*, may be employed in the combined vaccines of this invention. Similarly, other conventional adjuvants and inactive vaccine components may be employed in the formulations and selected by one of skill in the art. The dosages and administration protocols for use of these vaccine compositions may also be adjusted by one of skill in the art based on the animal to be vaccinated, the disease for which protection is desired and other related factors. Such modifications and alterations to the compositions and processes of the present invention are believed to be encompassed in the scope of the claims appended hereto.

What is claimed is:

1. An alkaline-toxoided *Pateurella multocida* protein necrotizing toxin prepared by incubating a toxin extracted from a culture of a dermonecrotic necrotizing protein toxin producing strain of *P. multocida* whole cells at a temperature of between 12° and 19° C. under conditions of pH greater than about 10.5 for at least 12 hours, wherein said toxoid is capable of inducing production of an amount of antitoxin effective to neutralize the toxin.

2. The protein toxoid of claim 1 wherein the pH is about 10.5.

3. A vaccine composition comprising the alkaline-toxoided *P. multocida* protein necrotizing toxin of claim 1, and a carrier suitable for internal administration.

4. A method for detoxifying *Pasteurella multocida* necrotizing protein toxin which comprises extracting the necrotizing toxin from a culture of dermonecrotic necrotizing protein toxin producing strain of *Pasteurella multocida* whole cells and incubating the toxin at a pH of at least about 10.5 at a temperature of between about 12° and 19° C. for at least 12 hours.

5. The method according to claim 4 which further comprises adjusting the pH to between 6 and 8 following said incubation.

6. The method according to claim 4 which further comprises clarifying the lysate by centrifugation or microfiltration prior to or after said incubation.

\* \* \* \* \*